(12) United States Patent
Grubbs et al.

(10) Patent No.: US 6,306,988 B1
(45) Date of Patent: Oct. 23, 2001

(54) METHODS FOR CROSS-METATHESIS OF TERMINAL OLEFINS

(75) Inventors: Robert H. Grubbs, South Pasadena; Daniel J. O'Leary, Claremont, both of CA (US); Helen E. Blackwell, Somerville, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/491,800

(22) Filed: Jan. 26, 2000

Related U.S. Application Data

(60) Provisional application No. 60/117,270, filed on Jan. 26, 1999.

(51) Int. Cl.$^7$ ................................. C08F 4/26; C08F 4/60
(52) U.S. Cl. ..................... 526/172; 526/336; 502/155; 556/21; 556/22; 556/136
(58) Field of Search .................... 526/172, 336; 556/21, 22, 136; 502/155

(56) References Cited

U.S. PATENT DOCUMENTS 5,969,170 * 10/1999 Grubbs et al. ..................... 556/21

\* cited by examiner

*Primary Examiner*—David W. Wu
*Assistant Examiner*—R. Harlan
(74) *Attorney, Agent, or Firm*—Pillsbury Winthrop, LLP; Tanuja V. Garde

(57) ABSTRACT

A method for the cross-metathesis of terminal olefins is disclosed. The method describes making disubstituted internal olefin products by contacting a first terminal olefin with another first terminal olefin to form a dimer and then contacting the dimer with a second terminal olefin in the presence of a catalyst having the formula

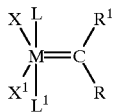

where M may be Os or Ru, R and $R^1$ may be the same or different and may be hydrogen or a substitutent group selected from $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, and $C_1$-$C_{20}$ alkylsulfinyl. X and $X^1$ may be the same or different and may be any anionic ligand. L and $L^1$ may be the same or different and may be any neutral electron donor.

19 Claims, No Drawings

METHODS FOR CROSS-METATHESIS OF TERMINAL OLEFINS

This application claims benefit of Provisional No. 60/117,270 filed Jan. 26, 1999.

The U.S. Government has certain rights in this invention pursuant to Grant No. GM 31332 awarded by the National Institute of Health.

BACKGROUND

The recent development of well-defined ruthenium and molybdenum metathesis catalysts has generated renewed interest in methods for selective cross-metathesis of terminal olefins. For example, Crowe et al. have demonstrated that π-substituted terminal olefins such as styrene and actylonitrile can be used to efficiently functionalized terminal olefins. Crowe has also reported a useful terminal olefin cross-coupling procedure utilizing nucleophillic species such as allyltrimethylsilane. More recently, Blechert et al. have shown that certain sterically hindered terminal olefins do not undergo self-metathesis and can be functionalized with a number of commercially available terminal olefins using ruthenium and molybdenum catalysts. The homologation of homoallylglycine derivatives has been reported by Gibson et al. Finally, both cross yne-ene and ring-opening cross metathesis reactions using Ru and Mo catalysts have been demonstrated. Unfortunately, these reactions tend to be slow, non-selective with relatively low product yields. As a result, large scale reactions for commercial applications are generally unfeasible using prior known methods.

SUMMARY OF THE INVENTION

The present invention relates to a method for making disubstituted internal olefin products from a first terminal olefin and a second terminal olefin. In general, the first terminal olefin is reacted with itself to form a dimer intermediate. The dimer is then reacted with the second olefin to yield the disubstituted internal olefin product. A schematic illustration of this concept is as follows:

$$XCH=CH_2 + XCH=CH_2 \rightarrow XCH=CHX + YCH=CH_2 \rightarrow XCH=CHY.$$

Dimerization of one of the initial terminal olefins unexpectedly results in faster rates of reaction, enhanced trans selectivity, and improved product yield.

DETAILED DESCRIPTION OF THE PREFERRED EMBODIMENTS

A typical reaction scheme for cross metathesis of two terminal olefins is as follows:

$$XCH=CH_2 + YCH=CH_2 \rightarrow XCH=CHY$$

wherein X and Y are independently an alkyl or aryl optionally substituted with one or more alkyl or aryl substituent groups. X and Y may also optionally include one or more functional groups. Illustrative examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

It has been unexpectedly discovered that dimerizing one of the initial terminal olefins results in faster rates of reaction, enhanced trans selectivity, and improved product yield. Dimerization to form a disubstituted olefin intermediate was inspired by the synthesis of telechelic polymers via ring opening polymerization/cross metathesis reaction as shown below.

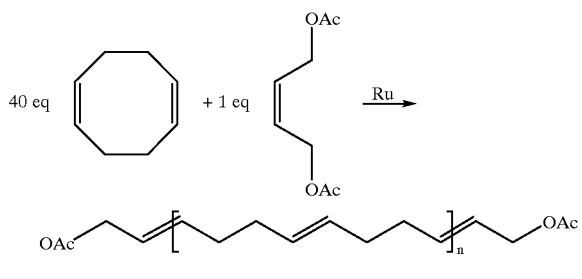

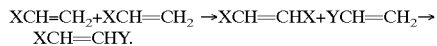

The present invention is a variation of this theme to make a disubstituted internal olefin product from a first terminal olefin and a second terminal olefin. As an initial matter, the first terminal olefin is reacted with itself to form a dimer. The dimer is then reacted with the second olefin to yield the disubstituted internal olefin product. A schematic illustration of this concept is as follows:

$$XCH=CH_2 + XCH=CH_2 \rightarrow XCH=CHX + YCH=CH_2$$
$$\rightarrow XCH=CHY.$$

Any suitable metathesis catalyst may be used. Illustrative examples of suitable catalysts include ruthenium and osmium carbene catalysts as disclosed by U.S. Pat. Nos.: 5,342,909; 5,312,940; 5,728,917; 5,750,815; 5,710,298, 5831,108, and 5,728,785, all of which are incorporated herein by reference. Briefly, the ruthenium and osmium carbene catalysts possess metal centers that are formally in the +2 oxidation state, have an electron count of 16, are penta-coordinated, and are of the general formula

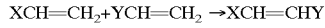

wherein:

M is ruthenium or osmium;

X and $X^1$ are each independently any anionic ligand;

L and $L^1$ are each independently any neutral electron donor ligand;

R and $R^1$ are each independently hydrogen or a substitutent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl. Optionally, each of the R or $R^1$ substitutent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_5$ alkoxy, and phenyl. Moreover, any of the catalyst ligands may further include one or more finctional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the R substitutent is hydrogen and the $R^1$ substitutent is selected from the group consisting $C_1$-$C_{20}$ alkyl, $C_2$-$C_{20}$ alkenyl, and aryl. In even more preferred embodiments, the $R^1$ substitutent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substitutent is phenyl.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula $PR^3R^4R^5$, where $R^3$, $R^4$, and $R^5$ are each independently aryl or $C_1$-$C_{10}$ alkyl, particularly primary alkyl, secondary alkyl or cycloalkyl. In the most preferred embodiments, L and $L^1$ ligands are each selected from the group consisting of -P(cyclohexyl)$_3$, -P(cyclopentyl)$_3$, -P(isopropyl)$_3$, and -P(phenyl)$_3$.

In preferred embodiments of these catalysts, X and $X^1$ are each independently hydrogen, halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, or $C_1$-$C_{20}$ alkylsulfinyl. Optionally, X and $X^1$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, X and $X^1$ are halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)(CH_3)_2CO$, PhO, MeO, EtO, tosylate, mesylate, or trifluoromethanesulfonate. In the most preferred embodiments, X and $X^1$ are each chloride.

For the purposes of clarity, the specific details of the present invention will be illustrated with reference to especially preferred embodiments. However, it should be appreciated that these embodiments and examples are for the purposes of illustration only and are not intended to limit the scope of the present invention.

A particularly useful application for the inventive method is in the homologation of terminal alkenes. The terminal alkene may be hindered or unhindered. As shown by Table 1, treatment of a terminal olefin such as 9-decen-1-yl benzoate (2a) with 1–2 equivalents of a symmetric internal olefin and 5 mol% ruthenium benzylidene 1 in refluxing dichloromethane provided the desired cross metathesis products in good yields. The reactions proceed largely to completion and the starting material homodimer can be easily recovered and recycled in a subsequent cross-metathesis step. In general, the inventive method favors the formation of the trans olefin isomer. For example, high trans selectivity was observed with cis-1,4-butenediol derivatives bearing bulky protecting groups.

Table 1 shows examples of cross metathesis reactions:

TABLE 1

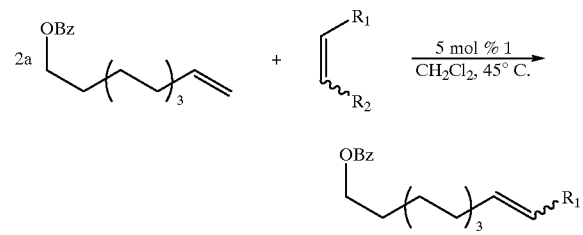

Table 1 shows examples of cross metathesis reactions:

| entry | substrate | equiv. | Product(%) | E/Z |
|---|---|---|---|---|
| 1 | $R_1 = R_2 = CH_2Oac$(cis) | 2 | 89 | 4.7:1 |
| 2 | $R_1 = R_2 = CH_2Oac$(cis) | 1 | 77 | 5:1 |
| 3 | $R_1 = CH_2Oac, R_2 = H$ | 4 | 81 | 3:1 |
| 4 | $R_1 = CH_2Oac, R_2 = H$ | 2 | 80 | 4:1 |
| 5 | $R_1 = CH_2Oac, R_2 = H$ | 1 | 59 | 5.7:1 |
| 6 | $R_1 = R_2 = CH_2OTBS$(cis) | 2 | 77 | 10:1 |
| 7 | $R_1 = R_2 = CH_2OtBu$(cis) | 2 | 90 | 7:1 |
| 8 | $R_1 = R_2 = CH_2OCH_2Ph$(cis) | 2 | 71 | 9:1 |
| 9 | $R_1 = R_2 = CH_2NHBoc$(cis) | 4 | 71 | 3:1 |
| 10 | $R_1 = R_2 = CH_2C(O)Ome$(trans) | 2 | 74 | 3.3:1 |

Table 1 charts the cross-metathesis product yields of example substrates. The percentage product yields (product (%)) reflects isolated product yields. The E/Z ratio was determined by $^1$H-NMR integration. Initial efforts focused upon the elaboration of terminal olefins to the corresponding allylic alcohol derivatives. The commercially available cis-2-butene-1,4-diol diacetate (entry 1) provided the homologated allylic acetate in excellent yield (89%, 4.7:1 E/Z) using two equivalents of internal olefin in refluxing dichloromethane. When only one equivalent of diacetate was used, the yield decreased (77%) and no significant change in the transcis ratio was observed (entry 2). The use of two equivalents of diacetate was found to be more efficient than simply using one, two, or four equivalents of allyl acetate (entries 3—5). Employing the diol acetate as solvent (55 equiv., 45° C., 12 h) increased the isolated yield to 91%, although with diminished trans olefin content (3:1 E/Z).

Good cross metathesis yields and improved trans selectivity were also found for several ether derivatives of cis-1,4-butenediol (entries 6-8). In entry 6,the 77% product yield was determined after TBAF deprotection of TBS ether. In entry 8, the 71% product yield was determined after $H_2$/Pd-C hydrogenation-hydrogenolysis of allyl benzyl ether. The compatibility of nitrogen-containing substrates was probed through the cross-metathesis of Boc-protected cis-1,4-diaminobutene (entry 9), which provides a direct route to protected allylic amines. Trans disubstituted internal olefins were also found to be reactive. Namely, dimethyl trans-3-hexene-1,6-dioate (entry 10) provided the desired homoallylic ester cross product as the major product (74%, 15 3:1 E/Z; recovered homodimer 3a: 23%). These results demonstrate that both cis or trans disubstituted internal olefins could be used as efficient coupling partners in cross metathesis reactions.

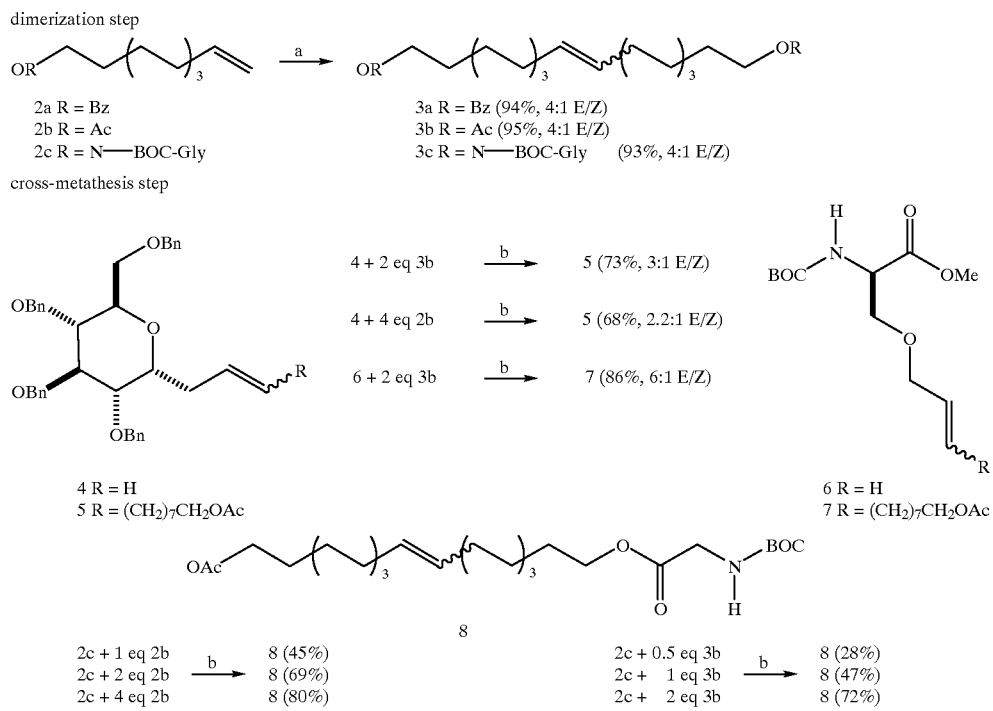

Dimerization of neat substances (2a–c) with 0.3 mol% 1 in vacuo provided mostly trans (4:1) disubstituted olefins in high yield. Homodimer 3b was subsequently used to functionalized 2,3,4,6-tetra-O-benzyl-1-α-C-allylglucoside (4) in 73% yield (3:1 e/Z recovered homodimer of 4: 19%). By comparison, the synthesis of 5 using four equivalents of terminal olefm 2b resulted in a marginally lower yield with slightly lower trans selectivity (68%, 2.2:1 E/Z). Olefin 3b was also used to successfully transform N-Boc-Serine-(O-Allyl)-OMe into lipophilic amino acid 7 in excellent yield and improved trans selectivity (85%, 6:1 E/Z). Cross coupling reactions using 9-decenyl-1-yl N-Boc glycinate (2c) and various equivalents of 9-decen-1-yl acetate (2b) or the internal olefin homodimer 3b demonstrate an advantage to adjusting the stoichiometry of a terminal olefin component in cross-metathesis reactions involving two isolated terminal olefins.

In sum, practice of the present invention results in the synthesis of disubstituted internal olefins in good yield and with improved trans selectivity. A particularly promising application of the inventive method is in the homologation of terminal olefins. The inventive method is also useful for the functionalization of advanced intermediates in multistep synthesis and for the construction of heterodimeric molecules for research in molecular biology.

EXPERIMENTAL METHODS

General Procedure for Solution-Phase Cross Metathesis Reactions.

An oven dried flask is charged with a magnetic stir bar and ruthenium benzylidene 1 (21 mg, 5 mol%) and capped with a septum under nitrogen atmosphere. $CH_2Cl_2$ (5 ml) and the disubstituted olefin (1.0 mmol, 2 equiv) are added in succession. The terminal olefin (0.5 mmol, 1 equiv) is added and the septum is quickly replaced with a condenser which is connected to a nitrogen bubbler. The flask is immersed in an oil bath and refluxed (bath temperature: 45° C.) for a period of 12 hours or until the reaction is judged complete by TLC.

The following publications and the references cited therein are incorporated herein in their entireties:

1. O'Leary et al., *Tetrahedron Letters* 1998, 39, 7427–7430.
2. Grubbs, R. H.; Chang, S. *Tetrahedron* 1998, 54, 4413–4450.
3. Crowe, W. E.; Zhang, Z. J. *J Am. Chem. Soc.* 1993, 115, 10998–0999.
4. Crowe, W. E.; Goldberg, D. R. *J. Am. Chem. Soc.* 1995, 117, 5162–5163.
5. Crowe, W. E.; Goldberg, D. R.; Zhang, Z. J. *Tetrahedron Lett.* 1996, 37, 2117–2120.
6. Brummer, O.; Ruckert, A.; Blechert, S. *Chem. Eur. J* 1997, 3, 441–446.
7. Gibson, S. E.; Gibson, V. C.; Keen, S. P. *Chem. Commun.* 1997, 1107–1108.
8. Stragies, R.; Schuster, M.; Blechert, S. *Angew. Chem., Intl. Ed. Engl.* 1997, 36, 2518–2520.
9. Randall, M. L.; Tallarico, J. A.; Snapper, M. L. *J. Am. Chem. Soc.* 1995, 117, 9610–9611.
10. Scheider, M. F.; Lucas, N.; Velder, J.; Blechert, S. *Angew. Chem., Intl. Ed. Engl.* 1997, 36, 257–259.
11. Hillmyer, M. A.; Nguyen, S. T.; Grubbs, R. H. *Macromolecules* 1997, 30, 718–721.
12. Schwab, P. E.; Grubbs, R. H.; Ziller, J. W. *J Am. Chem. Soc.* 1996, 118, 100–110, and Ulhnan, M.; Grubbs, R. H. *Organometallics* 1998, 17, 2484–2489.
13. Nubel, P. O.; Yokelson, H. B.; Lutman, C. A.; Bouslog, W. G.; Behrends, R. T.; Runge, K D. *J MoL Catal. A: Chem.* 1997, 115, 43–50.
14. Lewis, M. D.; Cha, J K.; Kishi, Y. *J Am. Chem. Soc.* 1982, 104, 4976–4978.

15. Sugano, H.; Miyoshi, M. *J Org. Chem.* 1976, 41, 2352–2353.

16. Diver, S. T.; Schreiber, S. L. *J Am. Chem. Soc.* 1997, 119, 5106–5109.

What is claimed is:

1. A method for making disubstituted internal olefin products comprising: contacting a terminal olefin with another terminal olefin to form a dimer; and contacting the dimer with a different terminal olefin in the presence of a catalyst of the formula:

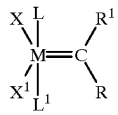

wherein:

M is ruthenium or osmium;

X and $X^1$ are either the same or different and are any anionic ligand;

L and $L^1$ are either the same or different and are any neutral electron donor;

R and $R^1$ are either the same or different and are each independently hydrogen or a substitutent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, wherein each of the substituents is substituted or unsubstituted.

2. The method of claim 1 wherein the substitutent group is substituted with one or more substituted or unsubstituted moieties selected from the group consisting of $C_1$-$C_{10}$ alkyl, $C_1$-$C_{10}$ alkoxy, and aryl.

3. The method of claim 2 wherein the moiety is substituted with one or more groups selected from the group consisting of halogen, $C_1$-$C_5$ alkyl, $C_1$-$C_5$ alkoxy, and phenyl.

4. The method of claim 1 wherein R is hydrogen and $R^1$ is selected from the group consisting of $C_1$-$C_{20}$ alkyl, $C_2$-$C_{20}$ alkenyl, aryl, unsubstituted phenyl, substituted phenyl, unsubstituted vinyl, and substituted vinyl; and wherein the substituted phenyl and substituted vinyl are each independently substituted with one or more groups selected from the group consisting of $C_1$-$C_5$ alky, $C_1$-$C_5$ alkoxy, phenyl, hydroxyl, thiol, ketone, aldehyde, ester, ether, amine, imine, amide, nitro, carboxylic acid, disulfide, carbonate, isocyanate, carbodiimide, carboalkoxy, and halogen.

5. The method of claim 1 wherein L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

6. The method of claim 1 wherein L and $L^1$ are each a phosphine of the formula $PR^3R^4R^5$ wherein $R^3$, $R^4$, and $R^5$ are each independently selected from the group consisting of aryl and $C_1$-$C_{10}$ alkyl.

7. The method of claim 6 wherein $R^3$, $R^4$, and $R^5$ are each independently selected from the group consisting of primary alkyl, secondary alkyl, and cycloalkyl.

8. The method of claim 6 wherein L and $L^1$ are each independently selected from the group consisting of P(cyclohexyl)$_3$, P(cyclopentyl) $_3$, P(isopropyl) 3, and P(phenyl) $_3$.

9. The method of claim 1 wherein X and $X^1$ are each independently selected from the group consisting of hydrogen, halogen, substituted moiety and unsubstituted moiety, wherein the moiety is selected from the group consisting of $C_1$-$C_{20}$ alky, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ allylsulfonyl, and $C_1$-$C_{20}$ alkylsulfinyl, and wherein the moiety substitution is selected from the group consisting of $C_1$-$C_{10}$ alkyl, $C_1$-$C_{10}$ alkoxy, and aryl.

10. The method of claim 9 wherein the moiety substitution is substituted with one or more groups selected from the group consisting of halogen, $C_1$-$C_5$ alkyl, $C_1$-$C_5$ alkoxy, and phenyl.

11. The method of claim 1 wherein X and $X^1$ are each independently selected from the group consisting of halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate.

12. The method of claim 1 wherein X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

13. The method of claim 12 wherein X and $X^1$ are both chloride.

14. The method of claim 1 wherein the terminal olefin used to form the dimer is of the formula $R^6CH=CH_2$ wherein $R^6$ is selected from the group consisting of $C_1$-$C_{50}$ alkyls and aryls, and wherein $R^6$ is substituted or unsubstituted.

15. The method of claim 14 wherein $R^6$ is substituted with one or more substituted or unsubstituted moieties selected from the group consisting of $C_1$-$C_{50}$ alkyls and aryls.

16. The method of claim 14 wherein $R^6$ is functionalized with one or more functional groups selected from the group consisting of hydroxyl, thiol, thioether, ketone, aldehyde, ester, ether, amine, amide, nitro, carboxylic acid, disulfide, carbonate, isocyanate, carboiimide, carboalkoxy, carbamate, and halogen.

17. The method of claim 1 wherein the different terminal olefin is of the formula $R^7CH=CH_2$, wherein $R^7$ is selected from the group consisting of $C_1$-$C_{50}$ alkyls and aryls, and wherein $R^7$ is substituted or unsubstituted.

18. The method of claim 17 wherein $R^7$ is substituted with one or more substituted or unsubstituted moieties selected from the group consisting of $C_1$-$C_{50}$ alkyls and aryls.

19. The method of claim 17 wherein $R^7$ is functionalized with one or more functional groups selected from the group consisting of hydroxyl, thiol, thioether, ketone, aldehyde, ester, ether, amine, amide, nitro, carboxylic acid, disulfide, carbonate, isocyanate, carboiimide, carboalkoxy, carbamate, and halogen.

* * * * *